(12) United States Patent
Park et al.

(10) Patent No.: US 9,962,315 B2
(45) Date of Patent: May 8, 2018

(54) ELECTRIC MODULE FOR STIMULATING SKIN

(75) Inventors: Chang-man Park, Seoul (KR); Chil Sung Lee, Suwon-si (KR); Changkeun Lee, Seoul (KR); Taehong Shin, Seoul (KR); Seunghwan Yi, Seoul (KR); Cheonghwan Hwang, Seoul (KR); Wooram Park, Seoul (KR); Kyung Shin Park, Seoul (KR); Jeongmin Lee, Suwon-si (KR); Byungyoung Kang, Seoul (KR)

(73) Assignees: AMOREPACIFIC CORPORATION, Seoul (KR); SENTRONIX CO., LTD., Suwon-si (KR)

( * ) Notice: Subject to any disclaimer, the term of this patent is extended or adjusted under 35 U.S.C. 154(b) by 449 days.

(21) Appl. No.: 14/238,887

(22) PCT Filed: Aug. 13, 2012

(86) PCT No.: PCT/KR2012/006440
§ 371 (c)(1),
(2), (4) Date: Feb. 14, 2014

(87) PCT Pub. No.: WO2013/027957
PCT Pub. Date: Feb. 28, 2013

(65) Prior Publication Data
US 2014/0200493 A1    Jul. 17, 2014

(30) Foreign Application Priority Data
Aug. 19, 2011   (KR) .......................... 10-2011-0082595

(51) Int. Cl.
*A61H 23/02*   (2006.01)
*A61N 1/32*    (2006.01)
*A61H 39/00*   (2006.01)

(52) U.S. Cl.
CPC ......... *A61H 23/02* (2013.01); *A61H 23/0254* (2013.01); *A61H 39/002* (2013.01);
(Continued)

(58) Field of Classification Search
CPC ................ A61H 23/02; A61H 23/0254; A61H 2201/0157; A61H 2201/10; A61H 2201/5005; A61H 39/002; A61N 1/325
See application file for complete search history.

(56) References Cited

U.S. PATENT DOCUMENTS 3,828,233 A * 8/1974 Brulard .................. H02P 7/281
318/376
5,036,422 A * 7/1991 Uchida .................. H01H 47/22
361/159
(Continued)

FOREIGN PATENT DOCUMENTS

EP      1163926 A1 * 12/2001 ............... A61N 1/30
JP      06-246008 A    9/1994
(Continued)

OTHER PUBLICATIONS

International Search Report of PCT/KR2012/006440 dated Feb. 18, 2013.

*Primary Examiner* — Valerie L Woodward
*Assistant Examiner* — Douglas Sul (57) ABSTRACT

Disclosed is an electrically-driven skin stimulation module for forming a relatively high potential difference between power terminals of different polarities without a voltage booster circuit to make a lot of current flow through human skin such that function of iontophoresis may be remarkably improved.

8 Claims, 7 Drawing Sheets

(52) U.S. Cl.
CPC ...... *A61N 1/325* (2013.01); *A61H 2201/0157* (2013.01); *A61H 2201/10* (2013.01); *A61H 2201/5005* (2013.01)

(56) References Cited

U.S. PATENT DOCUMENTS

| | | | | |
|---|---|---|---|---|
| 5,717,303 | A * | 2/1998 | Engel | B60L 7/003 307/56 |
| 7,127,285 | B2 * | 10/2006 | Henley | A61N 1/044 604/20 |
| 7,182,739 | B2 * | 2/2007 | Kopanic | A61F 7/03 601/15 |
| 7,349,733 | B2 * | 3/2008 | Joshi | A61N 1/0428 604/20 |
| 8,692,679 | B2 * | 4/2014 | Brickell | B66B 5/027 340/540 |
| 2004/0220622 | A1 * | 11/2004 | Bernabei | A61H 7/008 607/3 |
| 2012/0184884 | A1 * | 7/2012 | Dyer | A61H 19/50 601/46 |

FOREIGN PATENT DOCUMENTS

| | | |
|---|---|---|
| JP | 2004-209205 A | 7/2004 |
| JP | 2009-522064 A | 6/2009 |
| KR | 20-0219490 Y1 | 4/2001 |
| KR | 20-0276414 Y1 | 5/2002 |

* cited by examiner

ELECTRIC MODULE FOR STIMULATING SKIN

CROSS REFERENCE RELATED APPLICATION

This application claims foreign priority of Korean Patent Application No. 10-2011-0082595, filed on Aug. 19, 2011, which is incorporated by reference in its entirety into this application.

BACKGROUND OF THE INVENTION

1. Field of the invention

The present invention relates to an electric-driven skin stimulation module, and more particularly to an electrically-driven skin stimulation module for forming a relatively high potential difference between power terminals of different polarities without a voltage booster circuit to make a lot of current flow through human skin such that function of iontophoresis may be remarkably improved.

2. Description of the Prior Art

Human's desire for beauty is not basic instinct, so desires for clean and beautiful skin have made various efforts to manage skin and maintain youth along with human history. Especially among the desires for beauty, skin is a very importance object in desires to be a beauty and particularly face skin is one of importance factors determining a beautify appearance and a factor of affecting looks deeply.

Thus, regardless of genders or ages, most people give efforts to protect and manage their skin and various goods helpful to skin care are provided in order to satisfy these efforts. For example, there is a skin care device for improving absorption of cosmetics using activities of ions.

This skin care device using activities of ions is too expensive and big in size to buy and use. The existing skin care device has disadvantages that it is too complicated to manipulate and simple effect to use.

Meanwhile, there is a skin care device using low frequency so as to improve the disadvantages of the existing skin care device using ionic activities, such as a low frequency skin care device for varying output state of the low frequency to provide physical stimulation to skin and to remove waste matter from skin by the ionic activities, wherein this low frequency skin care device performs skin care using simply electrical stimulation by low frequency and the ionic activities, typically iontophoresis.

Iontophoresis is a method of increasing permeation of ionic medicine through human skin by forming a potential difference on human skin and changing electric circumstance of skin and has an important key of forming maximum current. That is, skin resistance of human body is very high, from several tens k$\Omega$ to several tens M$\Omega$, so that a relatively high input voltage higher than 15V is required to introduce a sufficient current into skin. Due to these reasons, the existing facial massage device using the iontophoresis usually includes a voltage booster circuit in an ion current generator, so that the ion current generator is complicated in structure, that overall size of the existing facial massage device increases, and that it is inconvenient to carry and keep in custody.

However, the existing skin care devices using iontophoresis use typically batteries as power supplies in order to obtain input voltage higher than 15V by booting voltage of the batteries, but to this end, additional boosting circuits are required and these make the existing skin care device more be complicated, bigger in volume, moreover increase in manufacturing cost.

SUMMARY OF THE INVENTION

Accordingly, the present invention has been made to solve the above-mentioned problems occurring in the prior art, and an object of the present invention is to provide an electrically-driven skin stimulation module for forming a relatively high potential difference between power terminals of different polarities without a voltage booster circuit to make a lot of current flow through human skin such that effect of iontophoresis may be improved.

The present invention also provides an electrically-driven skin stimulation module in which boosting between power terminals that are in direct contact with human skin is carried out using current of induced electromotive force generated from a coil of a rotary shaft without an external power supply nor a battery, so that consumption of the battery can be minimized.

The present invention also provides an electrically-driven skin stimulation module for transmitting vibration to skin through entire the electrically-driven skin stimulation module to human skin resulting in expansion of vibration transmission region and removal of a complicated boosting circuit so that overall volume thereof can be reduced and that mobility can be improved.

In order to accomplish this object, there is provided an electrically-driven skin stimulation module including: a base including power terminals of different polarities formed on a side to drive a vibrator and connected to each other through human skin as a conductor; the vibrator installed on at least one side of the base; a driving unit installed in the base and including a rotary shaft for providing a driving force to the vibrator and a coil interposing the rotary shaft therein; a driving switch installed at a power input end of the driving unit to switch on/off a power supply of the driving unit; a controller controlling the switching on/off of the driving switch to control operating state of the driving unit and vibration state of the vibrator according to the operation of the driving unit; and an induced electromotive force processor including an input end connected between the driving switch and the driving unit in parallel and making electric energy generated from the coil around the rotary shaft when the driving is idle by the switching off of the driving switch flow to an output end of the driving unit.

The controller controls the driving switch to switch on/off by a preset time interval in pulse width modulation (PWM).

Moreover, the driving unit includes a DC motor and the driving switch includes a transistor in which a driving voltage of the driving unit is supplied to an emitter and the pulse signal is applied to a base.

The induced electromotive force processor is a power diode.

The base is a printed circuit board on which the driving unit, the driving switch, the controller, and the induced electromotive force processor are mounted and which a circuit pattern for electrically connecting the components to each other is formed.

The printed circuit board is a flexible printed circuit board (FPCB).

An output voltage of maximum 13V and an output current of maximum 12 mA are discontinuously outputted from the power terminal of the base connected to the out end of the driving unit to the human skin.

The electrically-driven skin stimulation module further includes: a battery mounted on the base to supply an electric power to the driving unit and the controller; a power connection member electrically connecting power terminals of the battery to the power terminals of the driving unit of the base; and an insulator attached to a contact region between the power terminals of the battery and the power connection member to allow a contact between the power terminals of the battery and the power connection member when the insulator is removed from the battery.

The insulator is made in the form of a sheet and detachably attached to the battery to screen the power terminals.

According to an embodiment of the present invention, since a potential difference between the power terminals of different polarities is increased without a boosting circuit and by doing so a lot of current may flow through human skin so that effect of the iontophoresis can be maximized.

Moreover, since the boosting between the power terminals directly contacting human skin is carried out using induced electromotive force generated from a coil of the rotary shaft without a boosting circuit nor consumption of the battery, consumption of the battery can be minimized during the use of the electrically-driven skin stimulation module.

In addition, since vibration is transmitted to human skin through the entire electrically-driven skin stimulation module and the relatively complicated boosting circuit is not required, the area to which vibration is transmitted is relatively expanded and mobility thereof can be improved due to the relatively reduced overall volume thereof.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, an electrically-driven skin stimulation module according to preferred embodiments of the present invention will be described with reference to the accompanying drawings.

Figure 1:
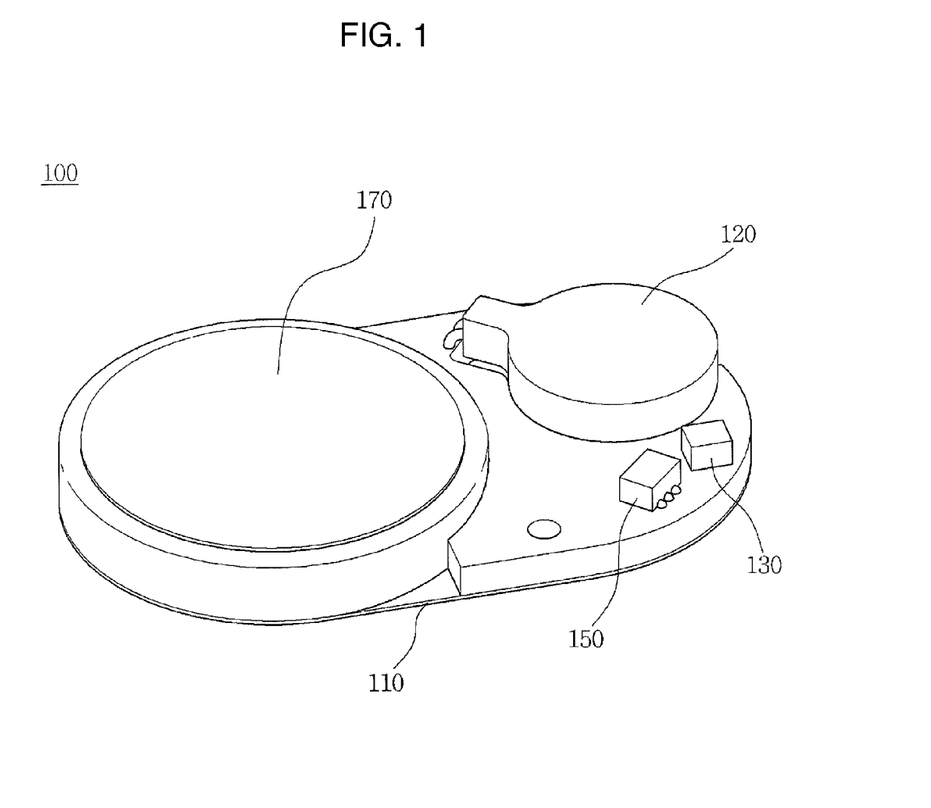
FIG. 1 is a perspective view illustrating an electrically-driven skin stimulation module according to an embodiment of the present invention.
Figure 2:
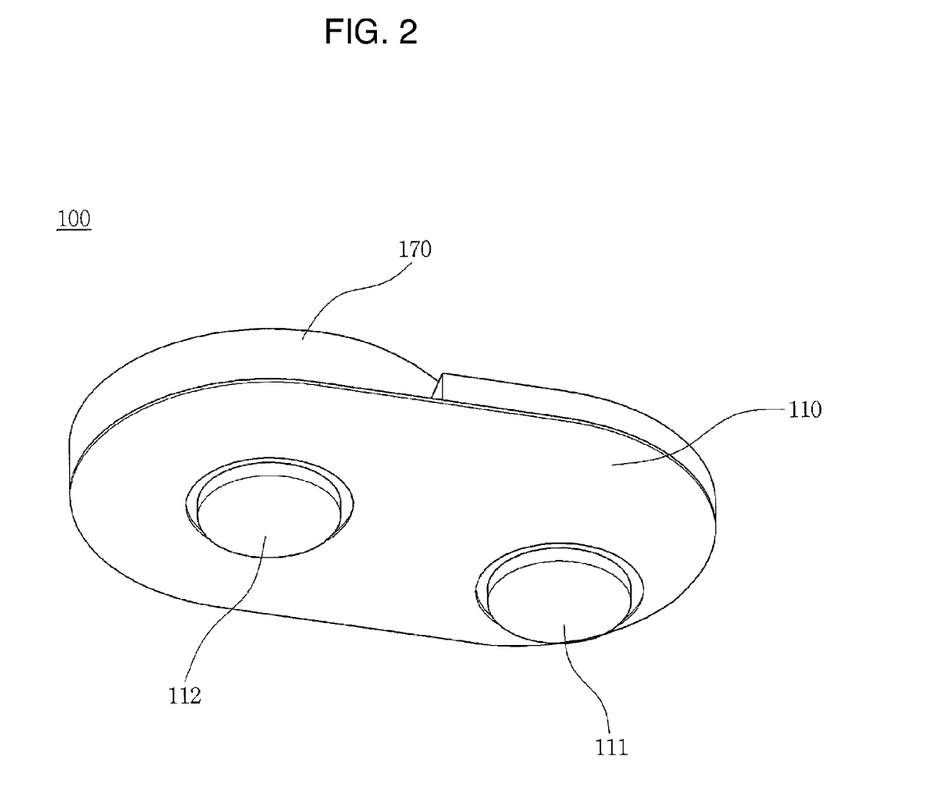
FIG. 2 is a rear perspective view illustrating an electrically-driven skin stimulation module according to the embodiment of the present invention.
Figure 3:
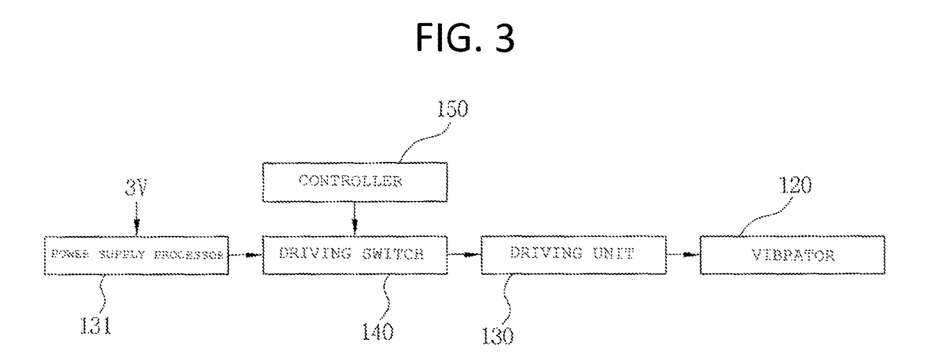
FIG. 3 is a block diagram illustrating the electrically-driven skin stimulation module according to the embodiment of the present invention.
Figure 4:
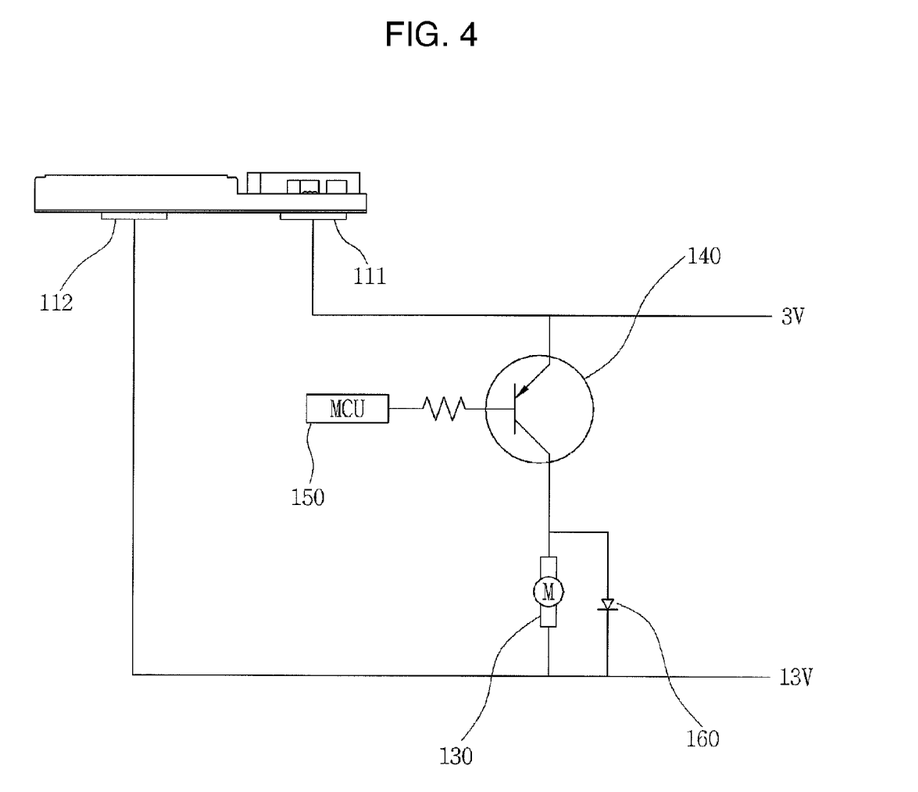
FIG. 4 is a view schematically illustrating a circuit in which an induced electromotive force of the electrically-driven skin stimulation module according to the embodiment of the present invention is processed.

FIG. 1 is a perspective view illustrating an electrically-driven skin stimulation module according to an embodiment of the present invention. FIG. 2 is a rear perspective view illustrating an electrically-driven skin stimulation module according to the embodiment of the present invention. FIG. 3 is a block diagram illustrating the electrically-driven skin stimulation module according to the embodiment of the present invention. FIG. 4 is a view schematically illustrating a circuit in which an induced electromotive force of the electrically-driven skin stimulation module according to the embodiment of the present invention is processed.

As illustrated, the electrically-driven skin stimulation module 100 according to the embodiment of the present invention includes a base 110, a vibrator 120, a driving unit 130, a driving switch 140, a controller 150, and an induced electromotive force processor 160.

The base 110 has power terminals 111 and 112 of different polarities installed on a side thereof and driving the vibrator 120. The power terminals 111 and 112 supply an electric power to the driving unit 130 driving the vibrator 120 to vibrate. Moreover, the power terminals 111 and 112 are connected to each other through human skin as a conductor and this is for iontophoresis of forming a potential difference on the human skin to change electric circumstance of the human skin and by increasing permeation of ionic medicine.

The vibrator 120 is installed on at least one side of the base 110 and vibrates in a preset pattern according to operation of the later-described driving unit 130. Vibrations of the vibrator 120 are transmitted to the base 110 so that whole the base 110 vibrates when the vibrator 120 vibrates.

The driving unit 130 is installed in the base 110 and includes a rotary shaft (not shown) providing driving force to the vibrator 120 and a coil interposing the rotary shaft therein. A DC motor is a typical example of the driving unit 130. Thus, although hereinafter the driving unit 130 will be described by a DC motor, the present invention is not limited thereto. A reference numeral 131 indicates a power supply processor installed in a power input end of the driving unit 130.

The driving switch 140 is installed at a power input end of the driving unit 130 and switches on/off to supply electric power to the driving unit 130 or to interrupt the electric power supplying to the driving unit 130. In this embodiment, the driving switch 140 is a transistor an emitter of which is supplied with a driving power, a base of which is supplied with a pulse signal from the controller 150. The present invention is not limited thereto, but the driving switch 140 may be various types satisfying conditions that a switch is on/off by a pulse signal to supply electric power to or interrupt power supplied to the driving unit 130. Moreover, in this embodiment the driving power supplied to the driving unit 130 is 3V.

The controller 150 controls ON/OFF of the driving switch 140 such that operating state of the driving unit 130 and vibration state of the vibrator 120 according to the operation of the driving unit 130 are controlled. The controller 150 controls the driving unit 130 in Pulse Width Modulation (PWM). That is, when a pulse signal of the controller 150 is applied to the base of the transistor, that is, the driving switch 140, the transistor repeats ON/OFF by preset time interval according to the pulse signal.

The induced electromotive force processor 160 includes an input end connected between the driving switch 140 and the driving unit 130 in parallel and an output end connected to an output end of the driving unit 1390 in parallel. The induced electromotive force processor 160 makes electric energy, which is generated by a coil around the rotary shaft of the driving unit 130, flow to the output end of the driving unit 130 when the driving unit 130 is idle by OFF operation of the driving switch 140. That is, DC motor as the driving unit 130 is driven when electric power is supplied by switching on of the driving switch 140 and still rotates due to the rotational inertia even when the driving switch 140 is switched off according to a pulse signal, while an induced electromotive force is generated at the coil of the DC motor.

The induced electromotive force generated at the coil of the DC motor is applied to an output end of the driving unit (DC motor) 130, and thus is applied to a minus (−) power terminal of the base 110 electrically connected to the output end of the driving unit 130 so that a relatively lot of current flows. In other words, a driving power of 3V is applied to the DC motor as the driving unit 130, that is, a voltage of a plus (+) power terminal of the base 110 is 3V while a voltage of the minus power terminal of the base 110 becomes 13V by the induced electromotive force applied from the coil of the DC motor.

Moreover, in this embodiment, although the induced electromotive force processor 160 is a power diode, the present invention is not limited thereto but the induced electromotive force processor 160 may be various types satisfying conditions that the induced electromotive force generated at the coil of the DC motor is applied to the output end of the DC motor.

In this embodiment, the base 110 is a printed circuit board on which the driving unit 130, the driving switch 140, the controller 150, and the induced electromotive force processor 160 are mounted and includes circuit patterns for the electric connection between the mounted components. The printed circuit board may be a flexible printed circuit board (FPCB) and this is to make the base 110 be easily attached to human skin along the contour of the human skin and vibration of the vibrator 120 be transmitted to the human skin more effectively.

As illustrated in FIGS. 1 to 4, due to the above-mentioned structure, the electrically-driven skin stimulation module 100 increases potential difference between the power terminals 111 and 112 of different polarities using the induced electromotive force generated at the coil of the DC motor without a voltage booster circuit so that more amount of current may flow through the human skin and that effect of the iontophoresis may be also improved.

Moreover, since the boosting of the power terminals 111 and 112 directly making a contact with the human skin is performed using current of the induced electromotive force generated from the coil of the rotary shaft without a voltage booster circuit nor consumption of the battery 170, consumption of the battery 170 can be minimized.

Moreover, since vibration is transmitted to the human skin through the entire electrically-driven skin stimulation module 100, a vibration transmission region extends and a relatively complicated voltage booster circuit is not needed so that overall volume of the electrically-driven skin stimulation module 100 is decreased and its mobility is improved.

Figure 5:
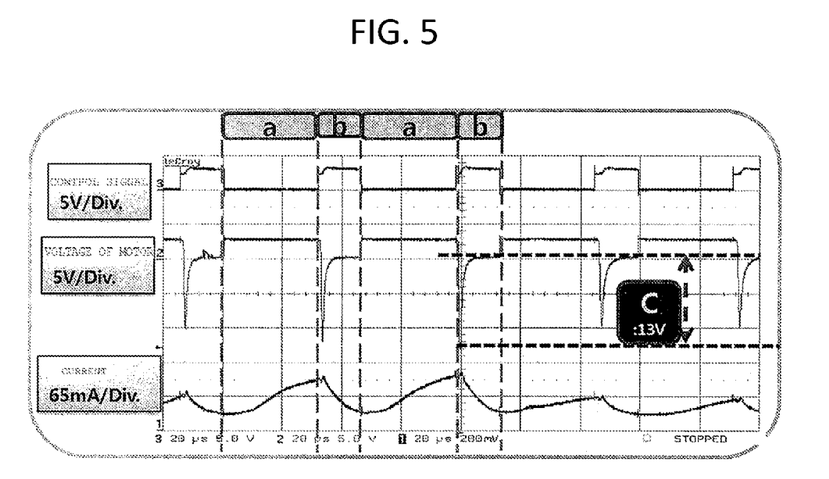
FIGS. 5 and 6 are graphs showing variation of an output voltage from a driving unit of the electrically-driven skin stimulation module according to the embodiment of the present invention.
Figure 6:
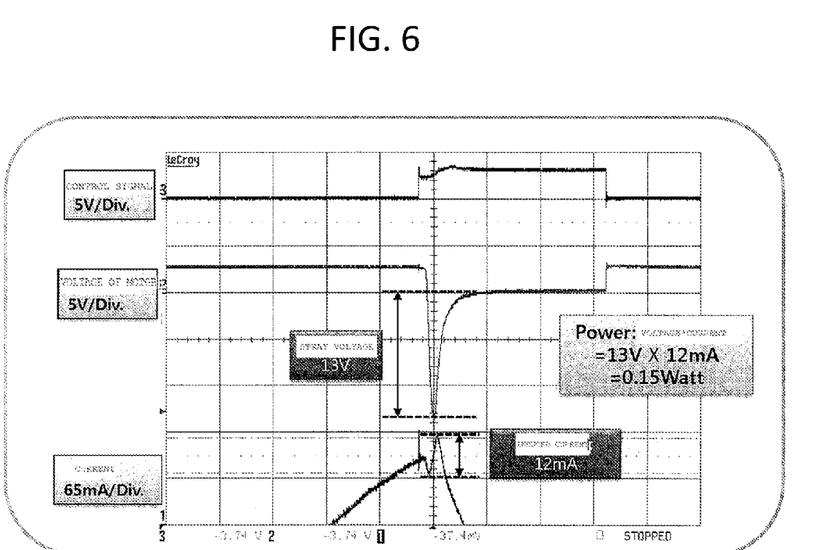

FIGS. 5 and 6 are graphs showing variation of an output voltage from a driving unit of the electrically-driven skin stimulation module according to the embodiment of the present invention.

Referring to FIG. 5, an electric power is supplied to the DC motor in a zone "a" and the electric power is not supplied to the DC motor in a zone "b". In this embodiment, a voltage of 5V is applied to the input end of the DC motor so that a pulse signal of 5V is applied from the controller 150 to the driving switch 140. A zone "c" indicates voltages of the induced electromotive force generated at the zone "b".

As illustrated, the induced electromotive force of maximum 13V is generated at the zone where an electric power is not supplied to the DC motor.

As illustrated in FIG. 6, as the induced electromotive force of maximum 13V is generated at the zone "b", it is confirmed that a current of maximum 12 mA flows through the human skin. In this case, the induced electromotive force and operation of the current to the human skin are applied in the form of discontinuous impulses and these operations are similar as acupuncture on the human skin, so that the human skin may be received with useful stimulation and that massage and treatment effect may be also provided.

Figure 7:
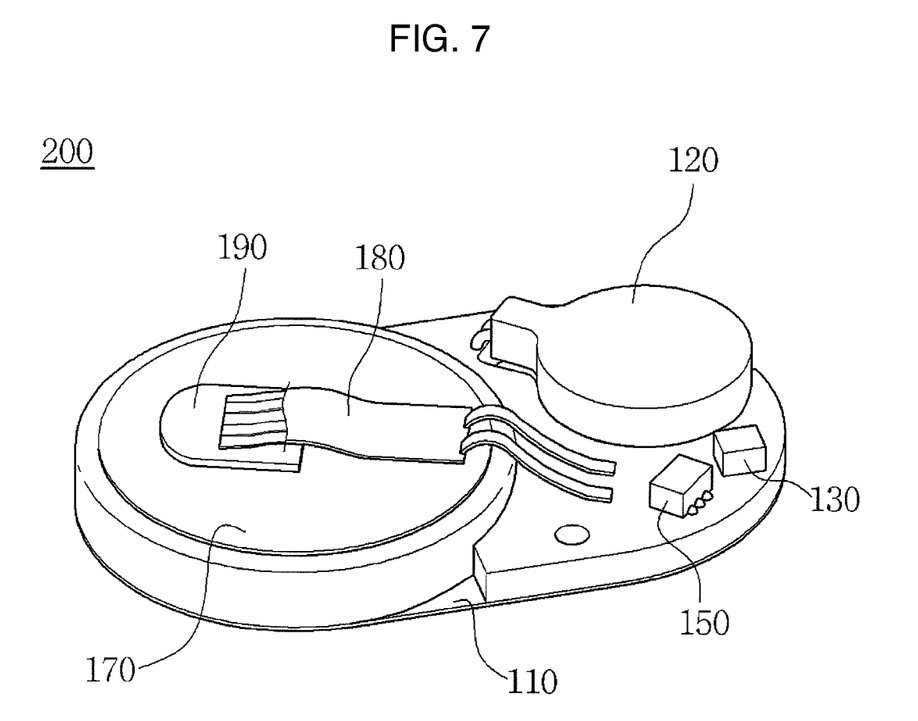
FIG. 7 is a perspective view illustrating an electrically-driven skin stimulation module according to another embodiment of the present invention.

Meanwhile, FIG. 7 is a perspective view illustrating a electrically-driven skin stimulation module according to another embodiment of the present invention. As illustrated, each of the electrically-driven module 200 includes a power connection member 180 and an insulator 190. The remaining components of the electrically-driven module 200 are identical to the electrically-driven module 100 according to the embodiment as illustrated in FIGS. 1 to 4 and thus their detailed descriptions will be omitted but same reference numerals are still used.

The battery 170 is installed in the base 110 and supplies electric power to the driving unit 130 and the controller 150 through the power connection member 180.

The power connection member 180 electrically connects power terminals (not shown) of the battery 170 to power terminals (not shown) of the driving unit 130 formed on the base 110. In other words, the driving unit 130 is electrically connected to the battery 170 through the power connection member 180. The power terminals of the base 110 may supply electric power to the controller 150, so that the base 110 includes circuit patterns connecting the power terminals to the driving unit 130 and the controller 150 in parallel.

The insulator 190 is attached to a contact area between the power terminals and the power connection member 180. That is, the insulator 190 is attached to the battery 170 to interrupt the electric connection between the power terminals of the battery 170 and the power connection member 180 and the electric connection between the power terminals of the battery 170 and the power connection member 180 is completed when the insulator 190 is removed from the battery 170. In this case, the insulator 190 is detachably attached to the battery 170 and the electric connection between the power terminals of the battery 170 and the power connection member 180 is controlled by the attachment and detachment of the insulator 190 to supply and interrupt the electric power to the driving unit 130.

That is, the insulator 190 may switch between the power terminals and the power connection member 180, while the electrically-driven skin stimulation module 200 may be configured such that the electric power of the battery 170 can be consumed only when to use by the switching function of the insulator 190 without a switch. In other words, the removal of a switch makes the electrically-driven skin stimulation module 200 be reduced in volume and the consumption of the battery 170 may be performed only when the vibrator 120 is driven.

Although in this embodiment the insulator 190 is a attachable thin seat to screen the power terminals of the battery 170, the present invention is not limited thereto but the insulator 190 may be changed and modified into various types under the conditions where the insulator 190 is detachably attached to the power terminal region of the battery 170 and supplies electric power between the power terminals of the battery 170 and the power connection member 180.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An electrically-driven skin stimulation module comprising:
    a base including power terminals of different polarities formed on a side to drive a vibrator and connected to each other through human skin as a conductor;
    the vibrator installed on at least one side of the base;
    a DC motor installed in the base and adapted to both (i) provide a driving force to the vibrator and (ii) induce an electromotive force for generating electrical energy to an output end of the DC motor;
    a driving switch installed at a power input end of the DC motor to switch on/off a power supply of the DC motor;
    a controller controlling the switching on/off of the driving switch to control operating state of the DC motor and vibration state of the vibrator according to the operation of the DC motor; and
    an induced electromotive force processor including an input end connected between the driving switch and the DC motor in parallel and making electric energy generated from the output end of the DC motor;
    wherein the output end of the DC motor is electrically connected to a power terminal of the base such that current flow in said power terminal is synchronized with the operation of the DC motor; and
    wherein an output voltage of maximum 13V and an output current of maximum 12 mA are configured to be discontinuously outputted from the power terminal of the base connected to the output end of the DC motor to the human skin.

2. The electrically-driven skin stimulation module as claimed in claim 1, wherein the controller controls the driving switch to switch on/off by a preset time interval in pulse width modulation (PWM).

3. The electrically-driven skin stimulation module as claimed in claim 1, wherein the driving switch comprises a transistor in which a driving voltage of the DC motor is supplied to an emitter and the pulse signal is applied to the base.

4. The electrically-driven skin stimulation module as claimed in claim 1, wherein the induced electromotive force processor comprises a power diode.

5. The electrically-driven skin stimulation module as claimed in claim 1, wherein the base comprises a printed circuit board on which the DC motor, the driving switch, the controller, and the induced electromotive force processor are mounted and which a circuit pattern for electrically connecting the components to each other is formed.

6. The electrically-driven skin stimulation module as claimed in claim 5, wherein the printed circuit board comprises a flexible printed circuit board (FPCB).

7. The electrically-driven skin stimulation module as claimed in claim 1, further comprising:
    a battery mounted on the base to supply an electric power to the DC motor and the controller;
    a power connection member electrically connecting power terminals of the battery to the power terminals of the DC motor of the base; and
    an insulator attached to a contact region between the power terminals of the battery and the power connection member to allow a contact between the power terminals of the battery and the power connection member when the insulator is removed from the battery.

8. The electrically-driven skin stimulation module as claimed in claim 7, wherein the insulator is made in the form of a sheet and detachably attached to the battery to screen the power terminals.

* * * * *